(12) United States Patent
Hajishah et al.

(10) Patent No.: US 10,993,837 B2
(45) Date of Patent: May 4, 2021

(54) MEDICAL DEVICE DATA FILTERING FOR REAL TIME DISPLAY

(71) Applicant: Johnson & Johnson Surgical Vision, Inc., Santa Ana, CA (US)

(72) Inventors: Abraham Hajishah, Irvine, CA (US); Mitchell W Mallough, Irvine, CA (US); Joseph E Pedroza, Vista, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 478 days.

(21) Appl. No.: 14/693,054

(22) Filed: Apr. 22, 2015

(65) Prior Publication Data
US 2015/0310171 A1    Oct. 29, 2015

Related U.S. Application Data

(60) Provisional application No. 61/983,329, filed on Apr. 23, 2014.

(51) Int. Cl.
*G06F 19/00*     (2018.01)
*A61F 9/007*     (2006.01)
(Continued)

(52) U.S. Cl.
CPC ............ *A61F 9/007* (2013.01); *A61B 3/0025* (2013.01); *A61B 3/0033* (2013.01);
(Continued)

(58) Field of Classification Search
CPC ... A61B 34/10; A61B 3/0025; G06F 3/04842; G06F 19/321
See application file for complete search history.

(56) References Cited

U.S. PATENT DOCUMENTS 6,280,436 B1 * 8/2001 Freeman ................. A61F 9/008
                                            128/898
7,135,016 B1 * 11/2006 Asia ........................ A61F 9/008
                                            606/12
(Continued)

FOREIGN PATENT DOCUMENTS

EP       1529504 A1    5/2005
WO    2015164467 A1   10/2015

OTHER PUBLICATIONS

Vision-Based Control of a Handheld Surgical Micromanipulator with Virtual Fixtures Brian C. Becker et. al.*
(Continued)

*Primary Examiner* — William L Bashore
*Assistant Examiner* — Nathan K Shrewsbury
(74) *Attorney, Agent, or Firm* — Johnson & Johnson Surgical Vision, Inc.

(57) ABSTRACT

An ocular surgical apparatus is provided, including a processor configured to receive ocular surgical data and a graphical user interface configured to display the ocular surgical data to a user. The processor configured to filter the ocular surgical data and the graphical user interface configured to display filtered ocular surgical data. The processor is configured to receive a number of ocular surgical data samples, discard selected ocular surgical data samples thereby yielding a number of emphasized samples, and perform an operation on the number of emphasized samples to produce filtered ocular surgical data.

27 Claims, 6 Drawing Sheets

(51) Int. Cl.
*A61B 34/10* (2016.01)
*A61B 3/00* (2006.01)
*G06F 3/0484* (2013.01)
*G16H 20/40* (2018.01)

(52) U.S. Cl.
CPC ............ *A61B 3/0041* (2013.01); *A61B 34/10* (2016.02); *G06F 3/04842* (2013.01); *G16H 20/40* (2018.01)

(56) References Cited

U.S. PATENT DOCUMENTS

| | | | |
|---|---|---|---|
| 8,092,023 B2* | 1/2012 | Korb | A61B 3/0025 351/206 |
| 2002/0115988 A1* | 8/2002 | Holladay | A61B 3/0025 606/5 |
| 2002/0161550 A1* | 10/2002 | Bharadwaj | F04D 29/661 702/182 |
| 2002/0183772 A1 | 12/2002 | Lieberman et al. | |
| 2003/0036751 A1* | 2/2003 | Anderson | A61B 5/0059 606/9 |
| 2003/0159141 A1* | 8/2003 | Zacharias | A61B 90/36 725/37 |
| 2004/0075807 A1 | 4/2004 | Ho et al. | |
| 2004/0097922 A1* | 5/2004 | Mullaney | A61B 17/6458 606/53 |
| 2004/0152990 A1* | 8/2004 | Mackool | A61F 9/00745 600/474 |
| 2004/0199480 A1* | 10/2004 | Unsworth | F04D 15/0077 706/16 |
| 2004/0267136 A1* | 12/2004 | Yaguchi | A61F 9/00745 600/459 |
| 2005/0057800 A1* | 3/2005 | Obrebski | A61B 90/50 359/385 |
| 2005/0253806 A1* | 11/2005 | Liberty | G06F 1/3215 345/156 |
| 2007/0027442 A1* | 2/2007 | Campin | A61B 3/152 606/12 |
| 2007/0146634 A1* | 6/2007 | LeBlanc | A61B 3/156 351/221 |
| 2008/0058782 A1* | 3/2008 | Frangineas | A61B 18/203 606/9 |
| 2008/0177256 A1* | 7/2008 | Loesel | A61F 9/00825 606/4 |
| 2008/0259279 A1 | 10/2008 | Pettit et al. | |
| 2008/0262571 A1* | 10/2008 | Greenberg | A61N 1/36046 607/54 |
| 2008/0263012 A1* | 10/2008 | Jones | G09C 1/00 |
| 2008/0287928 A1* | 11/2008 | Arnoldussen | A61F 9/00814 606/5 |
| 2008/0287929 A1* | 11/2008 | Holliday | G01N 33/04 606/5 |
| 2008/0319428 A1 | 12/2008 | Wiechmann et al. | |
| 2009/0306581 A1 | 12/2009 | Claus | |
| 2010/0069825 A1* | 3/2010 | Raney | A61B 17/320068 604/22 |
| 2010/0094262 A1* | 4/2010 | Tripathi | A61B 3/14 606/1 |
| 2010/0217278 A1* | 8/2010 | Tripathi | A61F 2/16 606/130 |
| 2011/0019151 A1* | 1/2011 | Schuhrke | A61B 3/111 351/206 |
| 2011/0092984 A1* | 4/2011 | Tripathi | A61B 3/13 606/130 |
| 2011/0158496 A1* | 6/2011 | Ciofolo-Veit | G06T 7/149 382/131 |
| 2011/0170060 A1* | 7/2011 | Gordon | A61B 3/156 351/206 |
| 2011/0224657 A1* | 9/2011 | Stevens | A61F 9/008 606/5 |
| 2011/0295617 A1* | 12/2011 | Berger | G16H 10/60 705/3 |
| 2011/0319875 A1* | 12/2011 | Loesel | A61F 9/00825 606/4 |
| 2012/0022546 A1* | 1/2012 | Hubschman | A61B 5/7415 606/107 |
| 2012/0095817 A1* | 4/2012 | Kamil | G06Q 30/0241 705/14.4 |
| 2013/0100409 A1* | 4/2013 | Grant | A61B 3/0025 351/221 |
| 2013/0109915 A1* | 5/2013 | Krupnik | G06F 3/0482 600/109 |
| 2013/0127984 A1* | 5/2013 | Grecu | H04N 5/23238 348/36 |
| 2013/0339891 A1* | 12/2013 | Blumenberg | G01C 21/3694 715/771 |
| 2014/0039510 A1* | 2/2014 | van Saarloos | A61B 3/0025 606/107 |
| 2014/0058367 A1* | 2/2014 | Dantus | A61F 9/00802 606/6 |
| 2014/0063455 A1* | 3/2014 | Zhou | G01J 9/00 351/206 |
| 2014/0066704 A1* | 3/2014 | Blumenkranz | A61B 1/00052 600/103 |
| 2014/0142425 A1* | 5/2014 | Razzaque | A61B 34/20 600/424 |
| 2014/0148808 A1* | 5/2014 | Inkpen | A61B 17/1703 606/80 |
| 2014/0171959 A1* | 6/2014 | Yacono | G02B 21/0012 606/128 |
| 2014/0187967 A1* | 7/2014 | Wood | A61B 5/0077 600/473 |
| 2014/0285429 A1* | 9/2014 | Simmons | G02B 27/0172 345/156 |
| 2014/0371762 A1* | 12/2014 | Farritor | A61B 34/30 606/130 |

OTHER PUBLICATIONS

International Search Report for Application No. PCT/US2015/027021, dated Jun. 12, 2015, 4 pages.
Industrial Measurement 2013 Measuring Controlling Regulating, Greisinger electronic, Made in Germany, A Subsidiary of GHM Messtechnik, 8 pages. (This document is a subset of the entire catalog).
Megatron-S3, X:\Projekte\S3\Doku\Patent_Einspruch_200909\s3_komm.sch,2020, 1 page.
Ophthalmic Surgical Instruments, Edition 1/04, Geuder, Precision made in Germany, Geuder AG Manufacturer of Ophthalmic Surgical Instruments and Systems, English Version, 10 pages.

* cited by examiner

MEDICAL DEVICE DATA FILTERING FOR REAL TIME DISPLAY

CROSS REFERENCE TO RELATED APPLICATION

This application claim priority to U.S. Provisional Application No. 61/983,329, filed on Apr. 23, 2014, entitled "Medical Device Data Filtering for Real Time Display," the entirety of which is incorporated by reference as if set forth herein.

BACKGROUND

Field of the Invention

The present invention relates generally to the field of surgical devices, and more specifically to the enhanced display of surgical information during surgical procedures.

Description of the Related Art

Ocular surgical procedures include phacoemulsification, diathermy, and vitrectomy procedures.

Phacoemulsification refers to a method of lens and cataract extraction from an eye. The procedure includes an ultrasonically vibrated needle which is inserted through a very small incision in the cornea in order to provide energy for fragmenting the lens and cataract which then can be aspirated and removed through the incision.

Diathermy refers to a method of cautery to seal severed or ruptured blood vessels. Diathermy is used in ophthalmic surgery to halt bleeding associated with surgical incisions Vitrectomy surgery has been successfully employed in the treatment of retinal detachments resulting from tears or holes in the retina. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port.

Both phacoemulsification and vitrectomy procedures employ highly sophisticated machinery designed to perform a variety of surgery related functions. Such procedures entail machinery controlling a handpiece used to cut and facilitate removal of ocular material and controlling the flow of fluid to and from the ocular region. Data is continuously monitored and various values are available to both ensure adequate operation of the machinery during the surgical procedure and provide information to a surgeon such that she can successfully perform the procedure while encountering changing conditions.

Both phacoemulsification and vitrectomy may employ a graphical user interface (GUI) that enables selection of parameters and displays current circumstances or parameters. Parameters monitored may include, but are not limited to, handpiece speed, fluid flow rate (both aspiration and irrigation), fluid pressure (both aspiration and irrigation), current mode, current submode, height of fluid bottle, time values, patient values (e.g. pulse rate, body temperature, etc.) and so forth. Certain devices are being deployed that monitor and provide more information related to a medical procedure, so the foregoing list is not exhaustive and can include other values depending on the particular device.

Some of these readings or values may be relatively static during much of the surgical procedure, while at certain times the values may be changing rapidly. Additionally, certain values, such as pressures, may be constantly changing. It can be difficult or even impossible to read displayed data when data is rapidly changing, and seconds can be extremely critical. For example, a surgeon may ask operating room personnel for a fluid pressure being applied at a certain time, and within seconds or tenths of seconds the value may change significantly such that the individual cannot provide the surgeon with an accurate number.

As a result, it would be beneficial to provide a system or design that provides a relatively stable data readout on devices such as graphical user interfaces in an ocular surgical environment. Such a design would afford a surgeon or other operating room personnel an ability to rapidly determine existing conditions and parameters.

SUMMARY

Thus according to one aspect of the present invention, there is provided an ocular surgical apparatus including a processor configured to filter ocular surgical data and a graphical user interface configured to receive the ocular surgical data and display the ocular surgical data to a user. The processor is configured to receive a number of ocular surgical data samples, deemphasize selected ocular surgical data samples thereby yielding a number of emphasized samples, and perform an operation on the number of emphasized samples to produce filtered ocular surgical data.

According to another aspect of the present design, there is provided an ocular surgical apparatus including a graphical user interface and a processor. The processor is configured to receive ocular surgical data during an ocular surgical procedure and display the ocular surgical data on the graphical user interface using a format comprising at least one selected from the group consisting of a numerical representation and a graphical representation. The processor is configured to filter the ocular surgical data and display filtered ocular surgical data in the format. The processor is also configured to receive a number of ocular surgical data samples, deemphasize selected ocular surgical data samples thereby yielding a number of emphasized samples, and perform an operation on the number of emphasized samples to produce filtered ocular surgical data for display according to the format.

According to another aspect of the present design, there is provided an ocular surgical procedure including receiving ocular surgical data at a processor, filtering the ocular surgical data using the processor to form filtered ocular surgical data, and displaying the filtered ocular surgical data on a graphical user interface. Filtering the ocular surgical data includes identifying a predetermined number of ocular surgical data samples, deemphasizing selected ocular surgical data samples thereby yielding a number of emphasized samples, and performing an operation on the number of emphasized samples to produce the filtered ocular surgical data.

Other features and advantages of the present invention should be apparent from the following description of exemplary embodiments, which illustrate, by way of example, aspects of the invention.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for providing filtered data in a desired format to a user, such as a surgeon or other operating room personnel in an ocular surgical setting, i.e. a phacoemulsification or vitrectomy procedure. The present design seeks to identify perceived speed of data changes and display current data by taking a number of samples, deemphasizing certain samples, e.g. suspected to be noise, and performing a function or functions to the emphasized samples, followed by displaying the results in the desired format. The precise functions performed, including deciding how many samples to track, how many to discard and select, and what operations to perform on the emphasized samples may vary based on the speed of the data expected to be encountered. The result is a filtered ocular surgical data display in a desired format.

The present design will be discussed herein with a particular emphasis on a medical or hospital environment where a surgeon or health care practitioner performs. For example, an embodiment of the present design is a phacoemulsification surgical system that comprises an integrated high-speed control module for the vitrectomy handpiece. The surgeon may adjust or set the cutting speed via a graphical user interface (GUI) module or a foot pedal to control the high-speed pneumatic vitrectomy handpiece.

Figure 1:
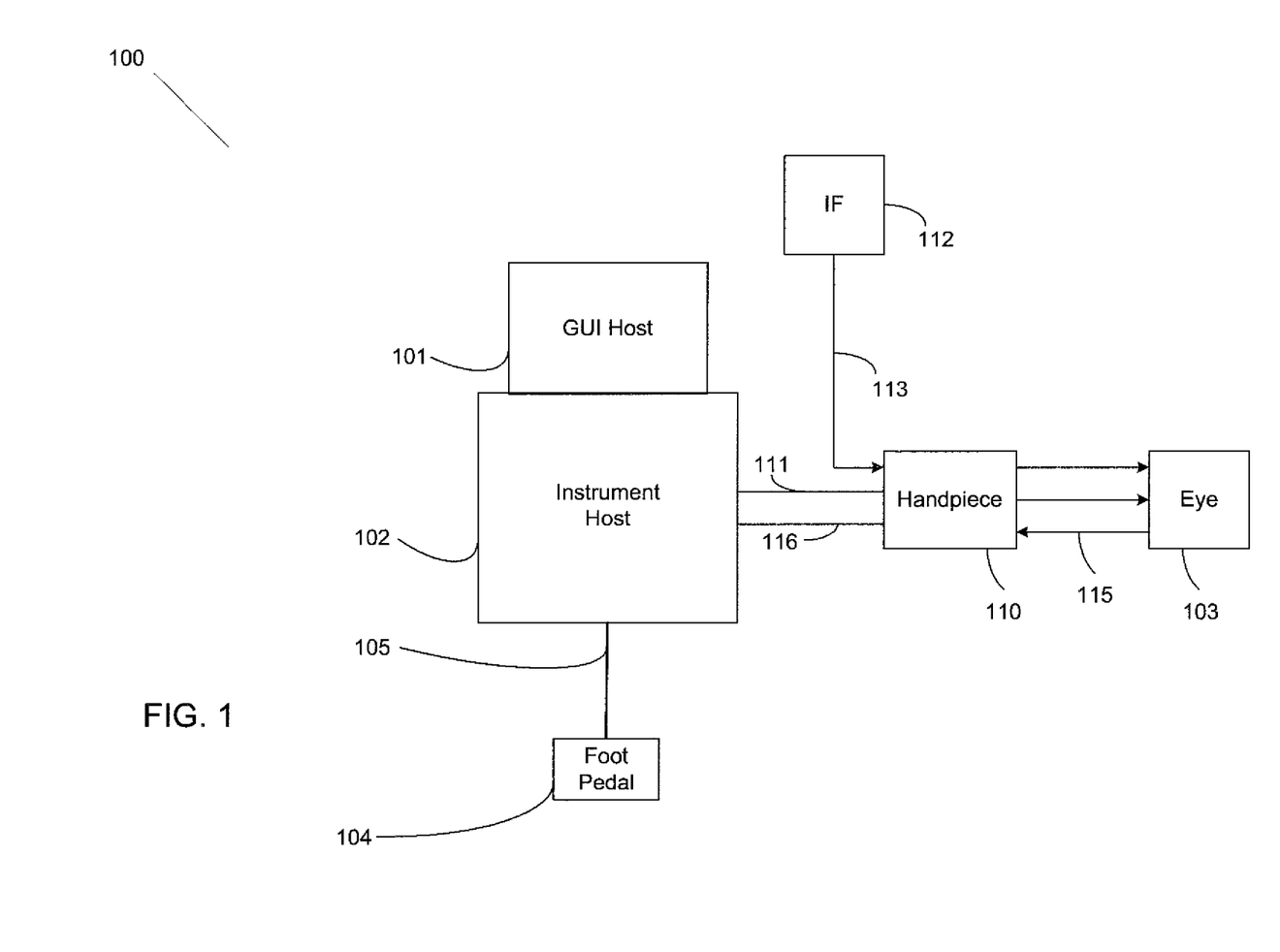
FIG. 1 is a block diagram illustrating an exemplary phacoemulsification/diathermy/vitrectomy system in accordance with an embodiment of the present design.

FIG. 1 illustrates an exemplary phacoemulsification/diathermy/vitrectomy system 100 in a functional block diagram to show the components and interfaces for a safety critical medical instrument system that may be employed in accordance with the present design. GUI host 101 and instrument host 102 reside on a single-board computer and communicate through inter-process communication. A processor (not shown) may be provided to control instrument host 102 and GUI host 101. Instrument host 102 typically takes the form of a computational device in the arrangement shown, but other arrangements are possible. An interface communications cable (not shown) may be connected to instrument host 102 for distributing instrument sensor data, and may include distribution of instrument settings and parameter information to other systems, subsystems and modules within and external to the instrument host 102. An interface communications cable may be connected or realized on any other subsystem (not shown) that could accommodate such an interface device able to distribute required data.

Foot pedal 104 may also be provided as part of phacoemulsification/diathermy/vitrectomy system 100. A switch module associated with foot pedal 104 may transmit control signals relating foot pedal physical and virtual switch position information as input to the instrument host 102 over serial communications cable 105. A wireless foot pedal may alternately be provided. Instrument host 102 may include a database file system for storing configuration parameter values, programs, and other data saved in a storage device (not shown).

Also shown in FIG. 1 is a handpiece 110 that is used for phacoemulsification and includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 103. Alternatively, the irrigation source may be routed to eye 103 through a separate pathway independent of the handpiece. Aspiration is provided to eye 3103 by a pump (not shown), such as a peristaltic pump and/or Venturi pump, via the instrument host 102, through lines 115 and 116. A surgeon/operator may select an amplitude of electrical pulses using the handpiece, or via the instrument host 102 and GUI host 101, or using footpedal 104.

GUI host 101 may display an assortment of data, images, and/or graphical representations on a graphical user interface (GUI), such as a touchscreen. During a surgical procedure, surgical parameters or values may be displayed on a GUI to indicate or notify a user of the maximum and minimum settings and/or the surgical parameters occurring at any point during the procedure, including, but not limited to vacuum, aspiration, foot pedal zone and pitch, and/or power. One example of a display arrangement that may be provided on a GUI is presented in FIG. 2, which includes a left border 201 including various selectable modes, a top border 202 including a number of selectable tabs, and in this view three sets of measurements, designated aspiration rate (element 203), vacuum pressure (element 204) and power (element 205). Each element includes settings, and in the configuration shown a touchscreen is provided such that the operator can increase or decrease the maximum or minimum settings, shown as 203a, 204a, and 205a in FIG. 2. The actual values of the parameters at any given time are shown as numerals 203b, 204b, and 205b, for example, respectively, an aspiration rate of 15 units, a vacuum of 75 units, and a power of 40 units. Units vary depending on the circumstances. Three "speedometer" type indications are also presented, namely graphical elements 203c, 204c, and 205c, where these graphical elements correlate with the numerical values provided in elements 203, 204, and 205.

Figure 2:
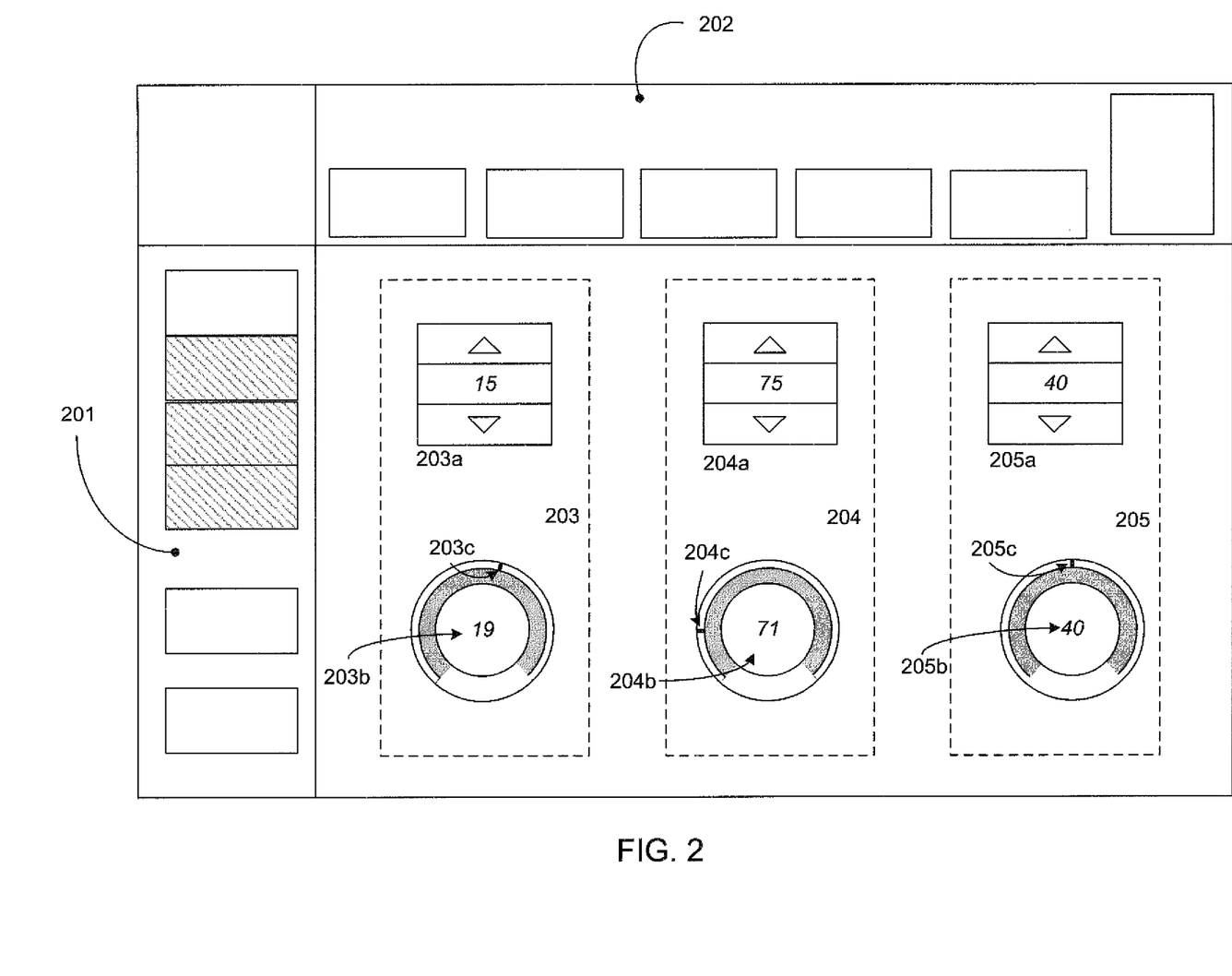
FIG. 2 illustrates a representative screen for a graphical user interface (GUI) usable in accordance with the present invention.
Figure 3:
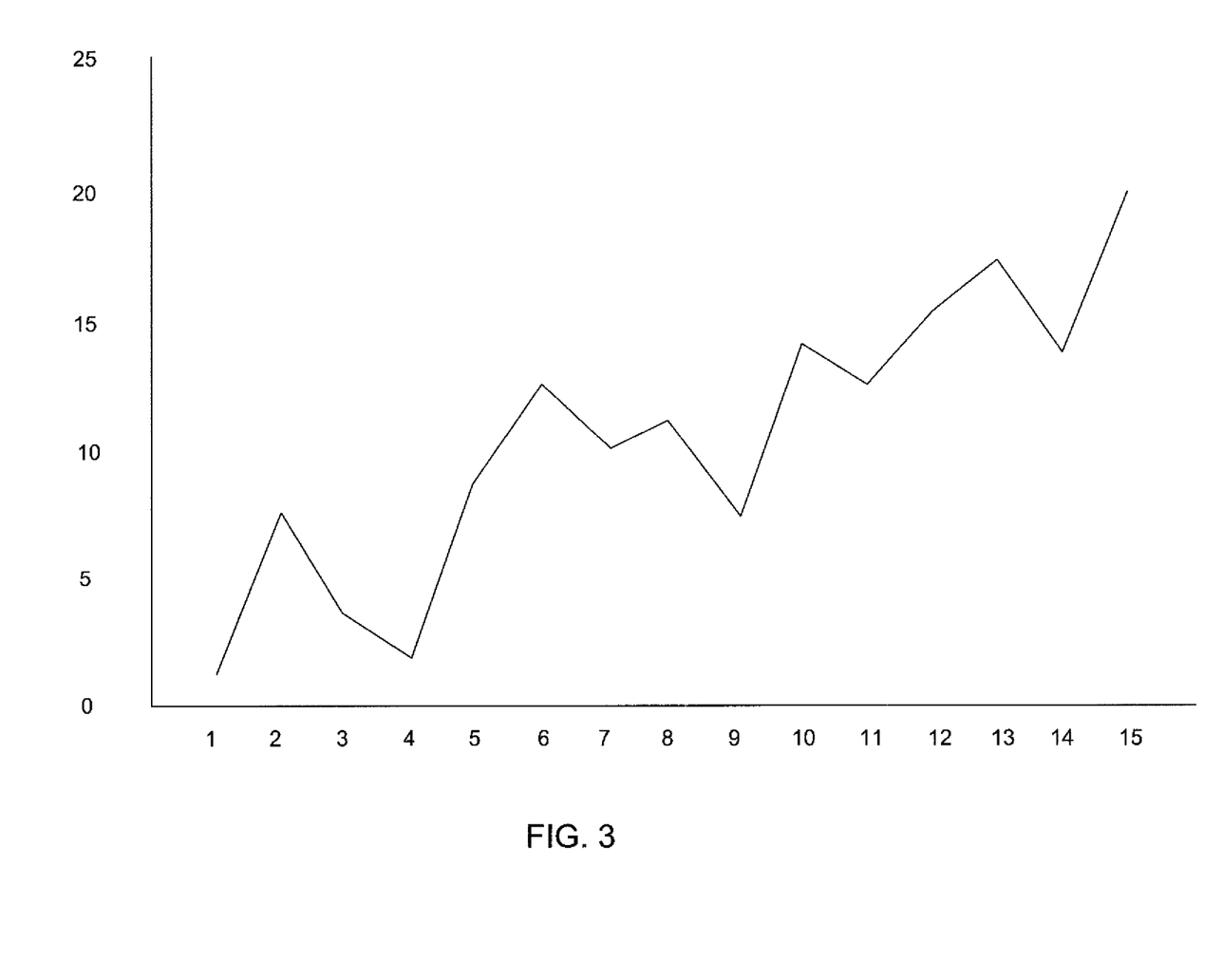
FIG. 3 illustrates representative noisy data.

A problem arises when the values are rapidly changing such that operating room personnel cannot accurately read either numerals 203b, 204b, or 205b, or graphical elements 203c, 204c, or 205c. FIG. 3 illustrates a representative graph of raw input data that might be encountered over a number of frames, with time as the x-axis and the value of the parameter provided as the y-axis. The graph of FIG. 3 shows significant fluctuations in the raw data, resulting in a jittery data display that can be difficult to read.

Faced with the data of FIG. 3, the system may take into account various factors, including but not limited to speed at which data is expected to change under normal conditions, speed at which data is expected to change under unusual conditions, i.e. in certain instances the data can drop X amount over Y frames but otherwise the data is expected to be fairly stable, and other parameters having to do with expected values, standard deviations, maxima and minima, and particular issues with the expected data. Based on expected performance, the present design may operate to remove or deemphasize certain data, such as data suspected to be noise, and manipulate the remaining data to more smoothly display the requisite data. As an example, in the depiction of FIG. 3, the expected range of the data may be between zero and 25, and the data may change up to 5 units per frame. In this instance, the system may elect taking the most recent four readings, may discard, ignore, or deemphasize the highest and lowest values, and may average the two remaining values to filter the data. Alternately, the system may take the most recent four readings, may take the most recent reading and may discard the two readings differing most from the most recent reading, leaving the most recent reading and the reading closest to the most recent reading, and may skew the current reading by a certain amount, i.e. 33% toward the reading closest to the most recent reading.

In the present design, identifying samples for use and/or manipulation can occur in any manner desired, including discarding values, ignoring values, deemphasizing values, or otherwise. Deemphasizing may in certain instances include assigning weights to certain samples, where a weight of zero indicates the value is to be ignored completely. The term "deemphasize" or "deemphasizing" is employed with the intent to be interpreted broadly to mean any type of reduction in the number of samples by any methodology possible.

As may be appreciated, any number of filtering methods may be employed. It is one goal of the present design to employ recent data in at least some capacity, i.e. not overriding actually encountered values. Virtually any value can be filtered, including values such as foot pedal position, power, aspiration, cut rate, patient conditions (pulse temperature, etc.) and so forth, and other implementations outside the medical field are possible.

As a further example, if the data rapidly changes over time, ten or more samples may be collected and manipulated in some manner, such as by deemphasizing the five samples farthest from the most recent sample, and selecting the median of those remaining values. Again, the particular filtering, smoothing, calculations, and manipulations may be dictated by the data expected to be encountered. In certain instances, no filtering may be provided.

Filtering may be a feature that is optional to the user, and the user may be allowed to employ his desired values. The user may be prompted to select a number of samples to be monitored, e.g. 20 frames or 0.8 seconds, the scheme used to determine the reading displayed, or other pertinent parameters. Alternately, the system may be configured to prompt the user for values, such as: "What parameter do you wish to filter?" "What is the maximum value expected to be encountered during this procedure?" "What is the minimum value expected to be encountered during this procedure?" "Approximately how rapidly does the parameter change (1 second, 0.1 second, 0.01 second?)" "Do you want extreme filtering, mild filtering, or no filtering?" The system may receive these selections and may fashion an appropriate filtering profile. In addition to the foregoing examples, the present design may receive entries from a user indicating a filtering of aspiration pressure is desired, the values are expected to vary between 20 and 100 units, and vary approximately every 0.1 second, and thus the system may determine 10 samples are requested, and with an 80 unit range, deemphasizing two samples and averaging the remaining eight is desired. Other values may be employed or obtained.

The present design may also consider parameters that are slow to change except for certain periods of time. For example, cut speed may be somewhat constant over time, but can change rapidly and significantly when modes change. In this instance, cut speed may not be filtered in most situations, but when modes change from mode P to mode Q for example, the device may apply filtering according to a set of established requirements for a certain amount of time after entering mode Q.

Figure 4:
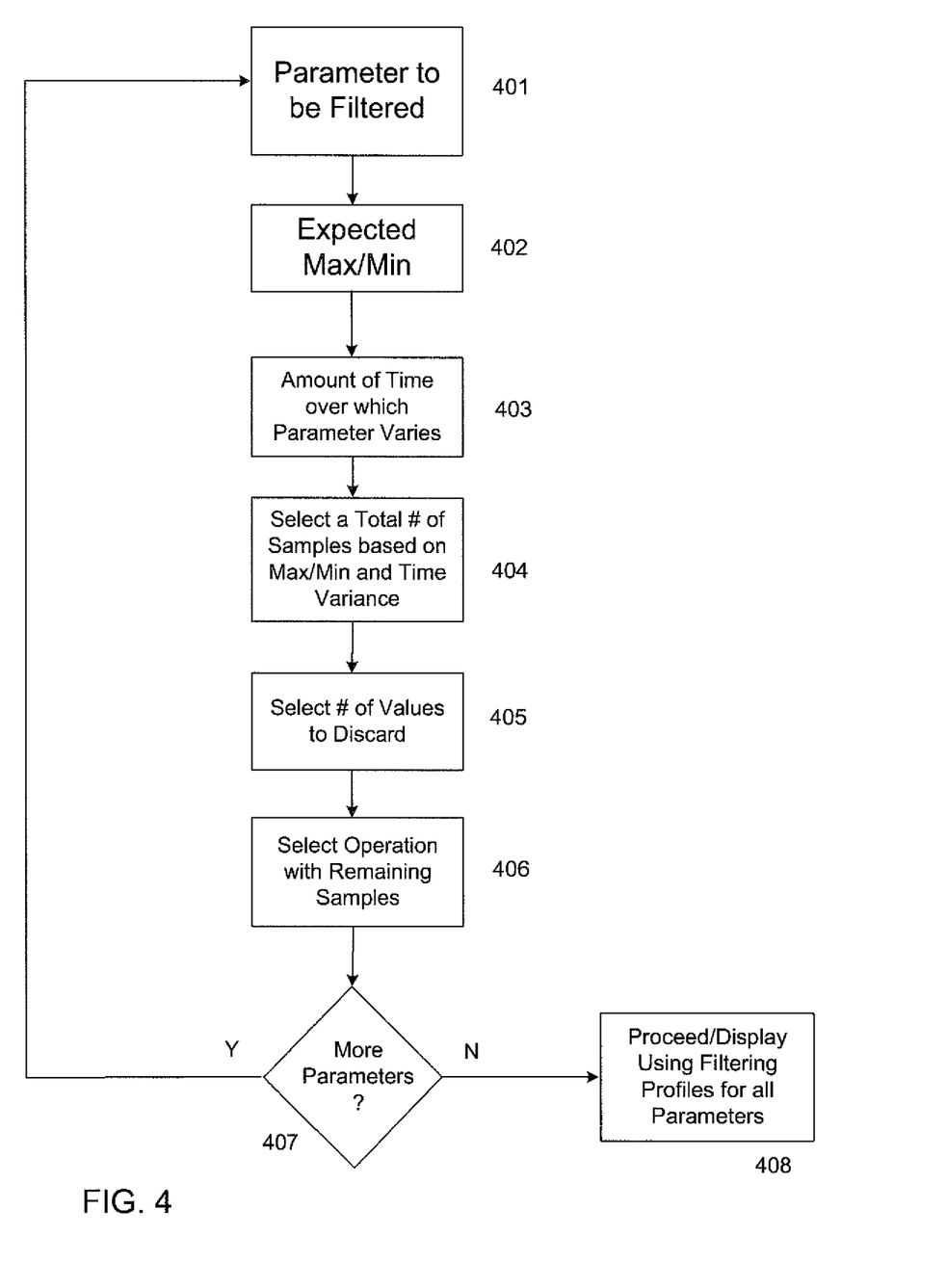
FIG. 4 is a general flowchart of operation according to one embodiment of the present design.

FIG. 4 illustrates a flowchart according to one embodiment of the present design. FIG. 4 is a flowchart operating without user intervention. The system initially determines the parameter to be filtered at point 401. At point 402, the system determines expected maximum and minimum values for the parameter, either using prior readings or based on values provided such as from a database. At point 403, the system determines the amount of time over which the parameter varies, again either using historical data or values from a database. Historical values may be determined in various ways, such as parameter X varies Y units over Z time on average, or using the maximum change of the parameter in the desired time frame, i.e. a worst case scenario where the parameter may change 20 units in less than 0.5 second. At point 404, the system selects the number of samples to be employed during filtering based at least in part on the maximum and minimum values and the amount of time over which the parameter changes or is expected to change. At point 405, the system selects a number of values or readings to discard and the specific samples or readings from the number of samples that will be discarded. Again, highest and lowest, furthest from the most recent sample, or other selection for deletion criteria may apply. Point 406 operates on the emphasized samples such that a value is determined, such as selecting an average, median, mean, most encountered value, or some other methodology.

At point 407, the system determines whether other parameters are to be filtered. If so, the system goes back to point 401. If no more parameters are to be filtered, the system proceeds to point 408, wherein display operation proceeds using the filtering profiles determined for all relevant parameters. In certain instances, no filtering may occur. For example, if the system is to filter patient temperature, but patient temperature tends to vary less than 0.1 degrees per minute, the determination at point 403 may result in too long a period of variance for the temperature parameter, and the system may elect no filtering is required. Again, FIG. 4 is an example, and different or alternate functionality may be provided to effectuate the filtering discussed herein.

Figure 5:
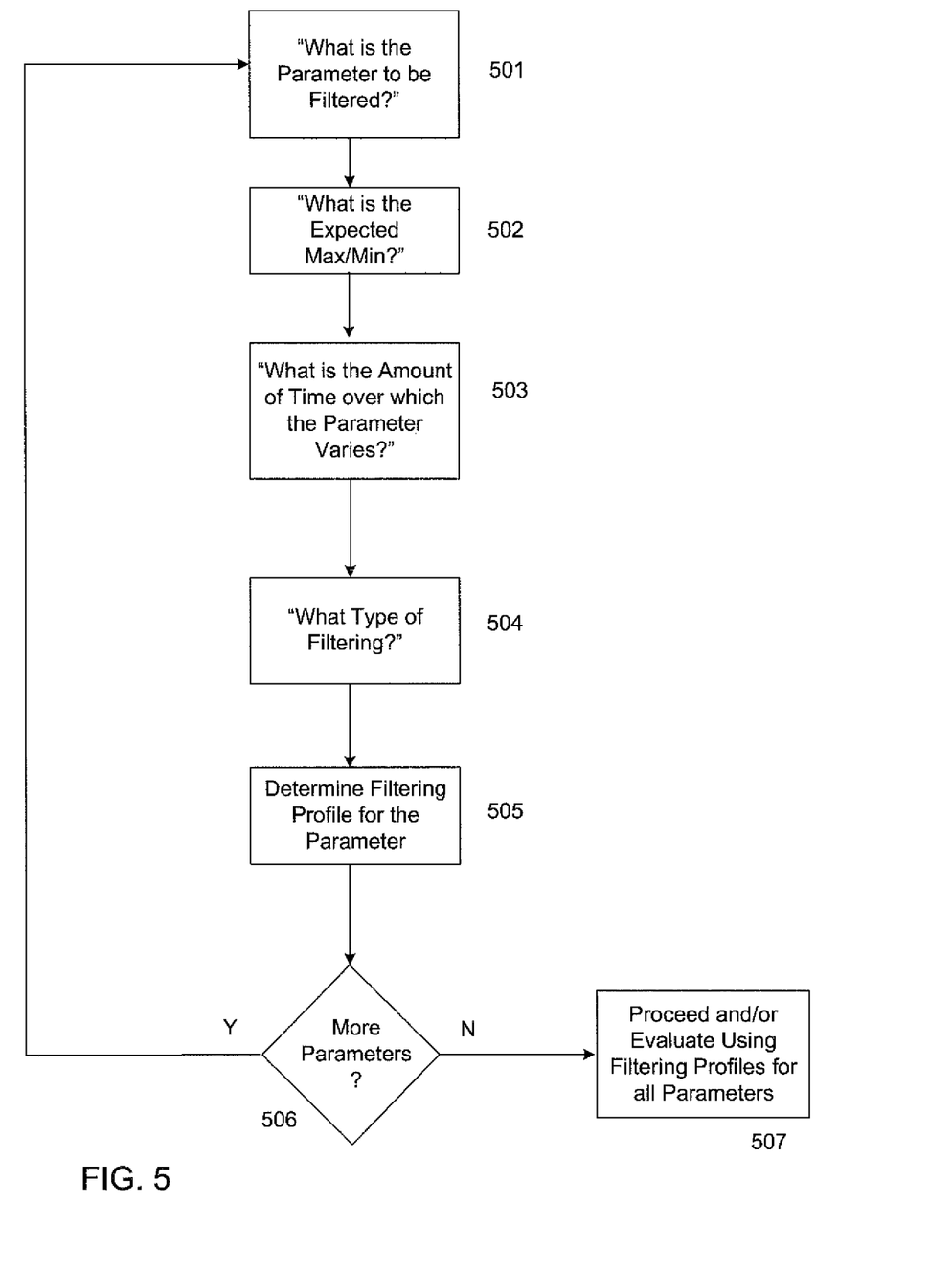
FIG. 5 shows a flowchart of a design according to an embodiment of the present design including user input.

FIG. 5 is a flowchart of a user assisted example of the present design. At point 501, the system prompts the user for a parameter to be filtered. At point 502, the system may prompt the user for an expected maximum and/or minimum value expected, while at point 503 the system prompts the user for the expected amount of time over which the parameter is expected to vary. This value is not required to be precise, and different values selected may provide different filtering results. Point 504 is optional and asks for the type of filtering, and different selections may be provided—mild or aggressive, a numerical scale, or other options. In general, the more aggressive filtering is required, the less the parameter will change over time. For no filtering, the raw data is displayed; for mild filtering, the raw data may be filtered such that the values appear to change more slowly than the raw data, and for aggressive filtering, the raw data is filtered such that the values appear to change much more slowly. Point 505 shows the system determining the precise filtering parameters, including the decision as to how many samples to employ, how many samples to discard, and how to process the emphasized samples. Point 506 prompts the user if more parameters are available, and if so, the system goes back to point 501. At point 507, the system may begin filtering and the user may evaluate the filtering provided.

Note that in the depiction or example of FIG. 5, the user may request different filtering parameters as time goes on, i.e. she may wish to remove filtering of cut rate at a certain point during the surgical procedure, or may wish to begin filtering aspiration rate at a particular time. Such functionality and ability to change filtering parameters or attributes may be provided to the user. Again, while FIG. 5 is an example of user-prompted operation, other parameters or functions may be employed, such as prompting the user for the number of samples to evaluate, the number of samples to discard, how to process the emphasized samples, and so forth. Other functionality is possible while still within the scope of the present invention.

Figure 6:
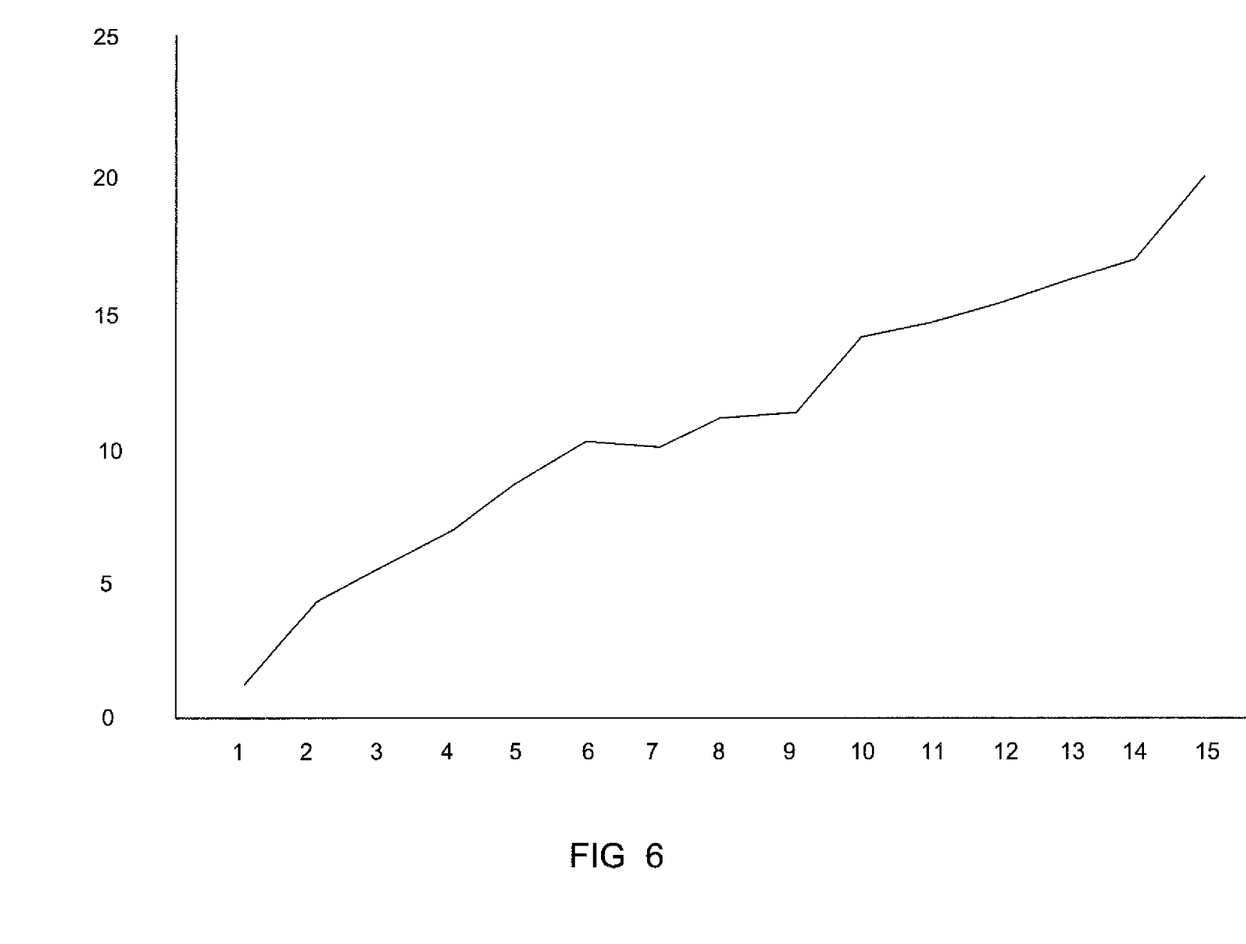
FIG. 6 is an example of data filtered according to the present design.

FIG. 6 shows a filtered version of the chart of FIG. 3. Such filtering provides a set of values that can be displayed and more easily assessed by the operating room staff.

In the present design, the GUI host 101 and the Instrument Host 102 may reside on a single board computer that may include a processor, storage device, and/or hardware that serves to provide the functionality described herein.

Thus the present design includes an ocular surgical apparatus including a processor configured to filter ocular surgical data and a graphical user interface configured to receive the ocular surgical data and display the ocular surgical data to a user. The processor is configured to receive a number of ocular surgical data samples, deemphasize selected ocular surgical data samples thereby yielding a number of emphasized samples, and perform an operation on the number of emphasized samples to produce filtered ocular surgical data.

Alternately, the present design includes an ocular surgical apparatus including a graphical user interface and a processor. The processor is configured to receive ocular surgical data during an ocular surgical procedure and display the ocular surgical data on the graphical user interface using a format comprising at least one selected from the group consisting of a numerical representation and a graphical representation. The processor is configured to filter the ocular surgical data and display filtered ocular surgical data in the format. The processor is also configured to receive a number of ocular surgical data samples, deemphasize selected ocular surgical data samples thereby yielding a number of emphasized samples, and perform an operation on the number of emphasized samples to produce filtered ocular surgical data for display according to the format.

One embodiment of the present design includes an ocular surgical procedure including receiving ocular surgical data at a processor, filtering the ocular surgical data using the processor to form filtered ocular surgical data, and displaying the filtered ocular surgical data on a graphical user interface. Filtering the ocular surgical data includes identifying a predetermined number of ocular surgical data samples, deemphasizing selected ocular surgical data samples thereby yielding a number of emphasized samples, and performing an operation on the number of emphasized samples to produce the filtered ocular surgical data.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, DOM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An ocular surgical apparatus comprising:
    a processor capable of filtering ocular surgical data based on a parameter; and
    a graphical user interface capable of receiving filtered ocular surgical data and displaying the filtered ocular surgical data to a user in real time;
    wherein the processor is capable of receiving ocular surgical data samples, determining a number of ocular surgical data samples to deemphasize based on an amount of variance of the parameter over an amount of time, selecting a subset of the ocular surgical data samples to deemphasize based on a deletion criteria and the number of ocular surgical data samples to deemphasize, deemphasizing the selected ocular surgical data samples thereby yielding emphasized samples from the ocular surgical data samples, and performing an operation on the emphasized samples to produce the filtered ocular surgical data;

wherein the graphical user interface is capable of displaying the filtered ocular surgical data to the user.

2. The ocular surgical apparatus of claim 1, wherein the graphical user interface is capable of receiving filtering parameters from a user, and the processor is capable of processing the filtering parameters received from the user.

3. The ocular surgical apparatus of claim 1, wherein the processor employs expected maximum and minimum values for ocular surgical data to be filtered.

4. The ocular surgical apparatus of claim 3, wherein the processor further employs an amount of time over which the ocular surgical data is expected to vary.

5. The ocular surgical apparatus of claim 1, wherein the operation comprises an averaging operation of the emphasized samples.

6. The ocular surgical apparatus of claim 2, wherein the graphical user interface is capable of receiving filtering parameters from the user during a surgical procedure.

7. The ocular surgical apparatus of claim 4, wherein the expected maximum and minimum values and the amount of time over which the ocular surgical data is expected to vary are based on prior readings.

8. The ocular surgical apparatus of claim 4, wherein the expected maximum and minimum values and the amount of time over which the ocular surgical data is expected to vary are obtained from a database.

9. An ocular surgical apparatus comprising:
a graphical user interface; and
a processor;
wherein the processor is capable of receiving ocular surgical data during an ocular surgical procedure and displaying the ocular surgical data on the graphical user interface using a format comprising at least one selected from the group consisting of a numerical representation and a graphical representation;
wherein the processor is capable of filtering received ocular surgical data and displaying the filtered ocular surgical data in the format in real time;
wherein the processor filtering the received ocular surgical data comprises receiving ocular surgical data samples, determining a number of ocular surgical data samples to deemphasize based on an amount of variance of the parameter over an amount of time, selecting a subset of the ocular surgical data samples to deemphasize based on a deletion criteria and the number of ocular surgical data samples to deemphasize, deemphasizing the selected ocular surgical data samples thereby yielding emphasized samples from the ocular surgical data samples, and performing an operation on the emphasized samples to produce the filtered ocular surgical data for display according to the format.

10. The ocular surgical apparatus of claim 9, wherein the graphical user interface is capable of receiving filtering parameters from a user, and the processor is capable of processing the filtering parameters received from the user.

11. The ocular surgical apparatus of claim 9, wherein the processor employs expected maximum and minimum values for ocular surgical data to be filtered.

12. The ocular surgical apparatus of claim 11, wherein the processor further employ s an amount of time over which the ocular surgical data is expected to vary.

13. The ocular surgical apparatus of claim 9, wherein the operation comprises an averaging operation of the emphasized samples.

14. The ocular surgical apparatus of claim 10, wherein the graphical user interface is capable of receiving filtering parameters from the user during the ocular surgical procedure.

15. The ocular surgical apparatus of claim 13, wherein the expected maximum and minimum values and the amount of time over which the ocular surgical data is expected to vary are based on prior readings.

16. The ocular surgical apparatus of claim 13, wherein the expected maximum and minimum values and the amount of time over which the ocular surgical data is expected to vary are obtained from a database.

17. An ocular surgical procedure comprising:
receiving ocular surgical data at a processor;
filtering the ocular surgical data using the processor to form filtered ocular surgical data; and
displaying the filtered ocular surgical data on a graphical user interface in real time;
wherein filtering the ocular surgical data comprises:
identifying a predetermined number of ocular surgical data samples;
determining a number of ocular surgical data samples to deemphasize based on an amount of variance of the parameter over an amount of time, selecting a subset of the ocular surgical data samples to deemphasize based on a deletion criteria and the number of ocular surgical data samples to deemphasize;
deemphasizing the selected ocular surgical data samples thereby yielding emphasized samples; and
performing an operation on the emphasized samples to produce the filtered ocular surgical data.

18. The ocular surgical procedure of claim 17, further comprising receiving filtering parameters from a user, and wherein filtering the ocular surgical data further comprises processing the filtering parameters received from the user.

19. The ocular surgical procedure of claim 17, wherein the filtering employs expected maximum and minimum values for ocular surgical data to be filtered.

20. The ocular surgical procedure of claim 17, wherein the filtering further employs an amount of time over which the ocular surgical data is expected to vary.

21. The ocular surgical procedure of claim 17, wherein the operation comprises an averaging operation of the emphasized samples.

22. The ocular surgical procedure of claim 18, further comprising receiving filtering parameters from the user during a surgical procedure.

23. The ocular surgical apparatus of claim 1, wherein the emphasized samples comprise a most recent sample.

24. The ocular surgical apparatus of claim 23, wherein the filtered ocular surgical data is based on the most recent sample.

25. The ocular surgical apparatus of claim 1, wherein the filtered ocular surgical data comprises a most recent sample.

26. The ocular surgical apparatus of claim 1, wherein the amount of variance of the parameter over an amount of time is selected from one of a speed at which data is expected to change under normal conditions and a speed at which data is expected to change under unusual conditions.

27. The ocular surgical apparatus of claim 1, wherein the selected ocular surgical data samples are a subset of the received ocular surgical data samples and wherein the emphasized samples are a subset of the received ocular surgical data samples.

\* \* \* \* \*